US006143704A

United States Patent [19]

[11] Patent Number: 6,143,704

[45] **Date of Patent: *Nov. 7, 2000**

Van Gunst et al.

[54] SOAP BARS WITH LITTLE OR NO SYNTHETIC SURFACTANT COMPRISING ORGANIC SALTS

[75] Inventors: Edward Andrew Van Gunst, Little Ferry, N.J.; James Joseph Corr, Dix Hills; John Gerard Sheehan, Brooklyn, both of N.Y.

[73] Assignee: Lever Brothers Company, Division of Conopco, Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/170,854

[22] Filed: Oct. 13, 1998

[51] Int. Cl.[7] .............................. A61K 7/50; C11D 17/00

[52] U.S. Cl. ........................... 510/152; 510/153; 510/155

[58] Field of Search .................................... 510/130, 141, 510/152, 153, 154, 155

[56] References Cited

U.S. PATENT DOCUMENTS

| | | | |
|---|---|---|---|
| 3,598,746 | 8/1971 | Kaniecki et al. . | |
| 4,169,067 | 9/1979 | Joshi . | |
| 4,288,341 | 9/1981 | Hooper et al. . | |
| 4,663,070 | 5/1987 | Dobrovolny et al. . | |
| 4,695,395 | 9/1987 | Caswell et al. . | |
| 5,030,376 | 7/1991 | Lee et al. . | |
| 5,194,172 | 3/1993 | Taneri et al. | 252/130 |
| 5,262,079 | 11/1993 | Kacher et al. | 252/112 |
| 5,264,145 | 11/1993 | French et al. | 252/117 |
| 5,387,362 | 2/1995 | Tollens et al. . | |
| 5,417,876 | 5/1995 | Tokosh et al. | 252/108 |
| 5,496,493 | 3/1996 | Cox et al. | 252/174 |
| 5,703,025 | 12/1997 | Zyngier et al. | 510/147 |

FOREIGN PATENT DOCUMENTS

| | | |
|---|---|---|
| 2317396 | 3/1998 | United Kingdom . |

*Primary Examiner*—Necholus Ogden
*Attorney, Agent, or Firm*—Ronald A. Koatz

[57] ABSTRACT

A bar composition comprising about 50–80% soap, about 4 to 35% by wt. free fatty acid and less than 5% synthetic surfactant. Addition of 1% to 10% organic salt has been found to allow use of little or no surfactant while maintaining consumer desirable properties.

9 Claims, No Drawings

SOAP BARS WITH LITTLE OR NO SYNTHETIC SURFACTANT COMPRISING ORGANIC SALTS

FIELD OF THE INVENTION

The present invention relates to predominantly soap bars, particularly those having little or no synthetic surfactant which process well while maintaining consumer desirable properties such as good color, good odor and good slip properties.

BACKGROUND OF THE INVENTION

Bar compositions comprising soap, synthetic surfactant (e.g., acyl isethionate), free fatty acid and organic salts (e.g., sodium isethionate, sodium citrate) are known in the art.

U.S. Pat. No. 4,663,070 to Dobrovolny et al. and U.S. Pat. No 4,695,395 to Caswell et al. for example, teach such compositions comprising 30% to 70% by wt. neat soap, 5% to 45% acyl isethionate, free fatty acid and sodium isethionate. By contrast, however, the amount of synthetic surfactant used in the compositions of the subject invention is less than 5%, preferably less than 4%, more preferably less than 3%, more preferably less than 2%, most preferably less than 1% by wt. and may be absent altogether. The amount of synthetic used in Dobrovolny is much higher.

U.S. Pat. No. 5,030,376 to Lee et al. also claims cleaning compositions comprising 20 to 80% fatty acid soap (mixture of tallow and coconut), 10% to 60% by wt. C8 to C18 fatty acyl isethionate and 1% to 6% by wt. electrolyte (e.g., organic salt) which may be sodium isethionate. Also, 1 to 20% free fatty acid is in the composition. Again, the synthetic surfactant comprises at least 10% by wt. composition in contrast to the amount of synthetic in the compositions of the invention being under 5%.

GB Patent 2,317,396 (to Cussons Int.) teaches bars with 30 to 90% soap, 1% to 35% secondary surfactant and combination of at least two materials which may be fatty acids, fatty alcohol and hydrocarbons of melting point above 25° C. (e.g., paraffin). There is no teaching or suggestion of adding the organic salts of the present invention in the GB patent.

In applicants copending application to Chambers et al., filed with British priority on Feb. 23, 1998, there is taught a specifically identified alkali metal soap; 3 to 35% fatty acid; 2 to 25% structurant; and water. There is no teaching of organic salts such as sodium isethionate or any teaching of the relationship between such salts and fatty acid in providing consumer benefits (as noted below).

Since synthetic surfactants (e.g., acyl isethionate, alkyl glycerol ether sulfate) are generally much milder than soap, one of the main reasons synthetic surfactant has been added to soap bars is to produce milder bars. The problem is that synthetic surfactants are also generally more expensive than soap.

One way of reducing the cost associated with synthetic surfactants is to replace some of the synthetic surfactant with free fatty acids. Such bars are known as superfatted bars. Unfortunately, substituting free fatty acid for synthetic surfactant, while this does possibly enhance mildness, may lead to the creation of bars with poorer user properties. Specifically, bars superfatted with long chain fatty acid, in the absence of the specific organic salts of the invention, tend to be tacky (e.g., extremely sticky, either to hands or equipment), to have noticeable discoloring and to have low lather.

In addition, a person of ordinary skill in the art would be disinclined to use any electrolyte (e.g., the specific organic salts of invention) in predominantly soap bar compositions because high (i.e., greater than 1%) levels of any electrolyte (e.g., organic or inorganic salts) have historically proven detrimental to the processability of these bars. Specifically, at high levels of, for example, sodium chloride, there is no cohesiveness between soap flakes formed when the flakes are extruded and the bars formed tend to become very brittle and "cracked" (see Comparative Examples 4 and 5).

In short, in the absence of the specific organic salts of the invention, there is no incentive to replace synthetic surfactant with free fatty acids because bars with little or no synthetic surfactant have poor user properties (especially in presence of a large amount of free fatty acid); yet there has been no incentive in the art thus far (in fact there has been teaching away) from using electrolyte of any kind (including organic salts) in such bars because high levels of electrolyte (e.g., inorganic alkali metal salts) are known to cause brittle bars which are difficult to process.

BRIEF SUMMARY OF THE INVENTION

Unexpectedly, applicants have now found that the use of specific organic salts (i.e., sodium isethionate, sodium citrate, sodium acetate) in such super-fatted, low synthetic surfactant compositions allow bars to be processed which are high lathering, have excellent bar slip, are low in mush, show excellent extrusion and stamping characteristics, and are generally milder than commercially marketed superfatted soaps (i.e., soap that generally tends to have larger amounts of free fatty acid). The bars are equivalent in consumer characteristics to currently marketed bars (i.e., Lever 2000®) which contained appreciable levels (at least 10%) of synthetic surfactant. The bars of the invention are less expensive (e.g., use less synthetic surfactant) and can be processed using standard soap processing equipment.

Since high levels of organic salts are used, minimum threshold levels of free fatty acid are required to ensure processability and user characteristics. In a preferred embodiment of the invention, the level of fatty acid is at least equal to the amount of organic salt; and the free fatty acid is more preferably a longer chain fatty acid (C16–C22). Mixtures of free fatty acid are of course contemplated and, when used, it is preferred the fatty acid mixture be predominantly (75%, preferably greater than 60%, more preferably greater than 50%) longer chain acid.

Specifically, the invention comprises (all percentages, unless otherwise noted, are by weight):

(1) about 50% to about 80%, preferably about 55%, more preferably greater than about 60% soap to about 80% soap;

(2) about 4% to 35%, preferably about 5% to 30%, more preferably 5% to 25%, more preferably 6% to 25%, more preferably 6% to 20% by wt. free fatty acid, where the free fatty acid is C8–C22, preferably C12–C18, more preferably C16–C18 fatty acid;

(3) about 1% to 10%, preferably 2% to 8% organic salt, preferably selected from the group consisting of alkali metal isethionate, alkali metal citrate, alkali metal acetate and mixtures thereof;

(4) 0% to 20% benefit agent; and where said composition comprises less than 5%, preferably less than 4%, preferably less than 3%, more preferably less than 2%, more preferably less than 1% and preferably no synthetic surfactant.

DETAILED DESCRIPTION OF THE INVENTION

The present invention relates to superfatted soap bar compositions (bars comprising predominantly soap and super-fatted with free fatty acid) containing low levels (less than 5%) of synthetic surfactant while maintaining low tackiness, good color and good lather.

The bars of the invention comprise about 50% to 80%, preferably 55% and more preferably greater than about 60% soap to about 80% soap.

The term "soap" is used herein in its popular sense, i.e., the alkali metal or alkanol ammonium salts of aliphatic, alkane-, or alkene monocarboxylic acids. Sodium, potassium, magnesium, mono-, di- and tri-ethanol ammonium cations, or combinations thereof, are suitable for purposes of this invention. In general, sodium soaps are used in the compositions of this invention, but from about 1% to about 25% of the soap may be potassium or magnesium soaps. The soaps useful herein are the well known alkali metal salts of natural of synthetic aliphatic (alkanoic or alkenoic) acids having about 8 to 22 carbon atoms, preferably about 8 to about 18 carbon atoms. They may be described as alkali metal carboxylates of acrylic hydrocarbons having about 8 to about 22 carbon atoms.

Soaps having the fatty acid distribution of coconut oil may provide the lower end of the broad molecular weight range. Those soaps having the fatty acid distribution of peanut or rapeseed oil, or their hydrogenated derivatives, may provide the upper end of the broad molecular weight range.

It is preferred to use soaps having the fatty acid distribution of coconut oil or tallow, or mixtures thereof, since these are among the more readily available fats. The proportion of fatty acids having at least 12 carbon atoms in coconut oil soap is about 85%. This proportion will be greater when mixtures of coconut oil and fats such as tallow, palm oil, or non-tropical nut oils or fats are used, wherein the principle chain lengths are C16 and higher. Preferred soap for use in the compositions of this invention has at least about 85% fatty acids having about 12 to 18 carbon atoms.

Coconut oil employed for the soap may be substituted in whole or in part by other "high-alluric" oils, that is, oils or fats wherein at least 50% of the total fatty acids are composed of lauric or myristic acids and mixtures thereof. These oils are generally exemplified by the tropical nut oils of the coconut oil class. For instance, they include: palm kernel oil, babassu oil, ouricuri oil, tucum oil, cohune nut oil, murumuru oil, jaboty kernel oil, khakan kernel oil, dika nut oil, and ucuhuba butter.

A preferred soap is a mixture of about 30% to about 40% coconut oil and about 60% to about 70% tallow. Mixtures may also contain higher amounts of tallow, for example, 15% to 20% coconut and 80 to 85% tallow.

The soaps may contain unsaturation in accordance with commercially acceptable standards. Excessive unsaturation is normally avoided.

Soaps may be made by the classic kettle boiling process or modern continuous soap manufacturing processes wherein natural fats and oils such as tallow or coconut oil or their equivalents are saponified with an alkali metal hydroxide using procedures well known to those skilled in the art. Alternatively, the soaps may be made by neutralizing fatty acids, such as lauric (C12), myristic (C14), palmitic (C16), or stearic (C18) acids with an alkali metal hydroxide or carbonate.

A second required component of the invention is free fatty acid. As noted above, this "superfat" traditionally would not be added in large amounts to bar compositions to replace synthetic surfactant (i.e., such that the bar is less than 5% synthetic surfactant) because it would cause bars to be tacky, suffer discoloration or have poorer lather. By tacky is meant that the bar product is sticky and leaves a residue on the hands when the dry bar or extruded log is touched. Sticky/tacky bars stick undesirably to extrusion equipment including chamber walls and press. Generally such bars will have reduced throughput. According to the subject invention, however, the fatty acid can be added in amounts ranging from 4% to 35%, preferably 5% to 30%, by wt. of the bar composition.

By free fatty acid is meant C8–C22, preferably C12–C18, more preferably C16–C18, preferably saturated, straight-chain fatty acids.

Of course the free fatty acids can be mixtures of shorter (e.g., C12–C14) and larger (e.g., C16–C18) chain fatty acids although it is preferred that longer chain fatty acids predominate over the shorter chain fatty acids.

A third required component of the invention is the use of specific organic salts (e.g., organic electrolytes) such as, for example, alkali metal (e.g., sodium) isethionate ($HOCH_2CH_2SO_3Na$), i.e., the sodium salt of 2-hydroxyethanesulfonic acid; alkali metal citrate; or alkali metal acetate (e.g., $CH_3COONa$).

Other organic salts include organic salts of aspartic acid (e.g., sodium aspartate), organic salts of acetic acid (e.g., sodium butoxyethoxyacetate), organic salts of D-gluconic acid (e.g., sodium gluconate), and sodium gluceptate. These organic salts are merely provided as examples and are not intended to limit the claims in any way.

Generally, organic salts are not intended to encompass salts derived from $C_8$–$C_{24}$ straight chain fatty acids, i.e., commonly known as "soaps". Also, alkali metal isethionate is not intended to encompass alkali metal salts of esters of isethionate, e.g., $R—CO_2CH_2CH_2SO_3—Na$ where R is long carbon chain.

Electrolytes, in particular sodium chloride which is necessary for soap making, are undesirable in large quantities in a soap bar because they will "short" the soap (make it grainy and unprocessable). In addition, other salts or electrolytes, organic or inorganic (i.e., sodium isethionate, etc.), will have a similar "shortening" effect if present in some threshold level in pure soap. While not wishing to be bound by theory, it is believed that in the presence of a minimal amount of fatty acid (as required by the invention), the shortening effect caused by the organic salts (such as those noted above) can be minimized or eliminated. That is, without fatty acid, the bars are unprocessable, crumbly, and brittle. However, where fatty acid is present, it synergizes with the organic salt to form a processable product. Moreover, the unexpected benefits of improved lathering, color, odor, and bar slip are observed.

It should be understood that small amounts (i.e., less than 3%) of alkali metal salts may be used in the composition of the invention as long as not so much is used that it will cause shortening effects described above.

The organic salts of the invention will generally comprise from 1% to 10%, preferably 2% to 8% by wt. of the composition. In preferred embodiments of the invention, the ratio of fatty acid to organic salt is 1:1 and higher.

The bars of the invention optionally comprise 0% to 20%, preferably 0.1% to 15%, more preferably 0.5% to 5%, more preferably 1% to 4% by wt. of a skin benefit agent.

The skin benefit agent of the subject invention may be a single benefit agent component or it may be a benefit agent compound added via a carrier. Further the benefit agent composition may be a mixture of two or more compounds, one or all of which may have a beneficial aspect. In addition, the benefit agent itself may act as a carrier for other components one may wish to add to the bar composition.

The benefit agent can be an "emollient oil" by which is meant a substance which softens the skin by increasing the water content.

Preferred emollients include:

(a) silicone oils, gums and modifications thereof such as linear and cyclic polydimethylsiloxanes; amino, alkyl alkylaryl and aryl silicone oils;

(b) fats and oils including natural fats and oils such as jojoba, soybean, rice bran, avocado, almond, olive, sesame, sunflower seed, persic, castor, coconut, mink oils; cacao fat; beef tallow, lard; hardened oils obtained by hydrogenating the aforementioned oils; and synthetic mono, di and triglycerides such as myristic acid glyceride and 2-ethylhexanoic acid glyceride;

(c) waxes such as carnauba, spermaceti, beeswax, lanolin and derivatives thereof;

(d) hydrophobic plant extracts;

(e) hydrocarbons such as liquid paraffins, vaseline, microcrystalline wax, ceresin, squalene, pristan and mineral oil;

(f) fatty acids such as lauric, myristic, palmitic, stearic, behenic, oleic, linoleic, linolenic, lanolic, isostearic and poly unsaturated fatty acids (PUFA);

(g) fatty alcohols such as lauryl, cetyl, stearyl, oleyl, behenyl, cholesterol and 2-hexydecanol alcohol;

(h) esters such as cetyl octanoate, myristyl lactate, cetyl lactate, isopropyl myristate, myristyl myristate, isopropyl palmitate, isopropyl adipate, butyl stearate, decyl oleate, cholesterol isostearate, glycerol monostearate, glycerol distearate, glycerol tristearate, alkyl lactate, alkyl citrate and alkyl tartrate;

(i) essential oils such as mentha, jasmine, camphor, white cedar, bitter orange peel, ryu, turpentine, cinnamon, bergamot, citrus unshiu, calamus, pine, lavender, bay, clove, hiba, eucalyptus, lemon, starflower, thyme, peppermint, rose, sage, menthol, cineole, eugenol, citral, citronelle, borneol, linalool, geraniol, evening primrose, camphor, thymol, spirantol, penene, limonene and terpenoid oils;

(j) lipids such as cholesterol, ceramides, sucrose esters and pseudo-ceramides as described in European Patent Specification No. 556,957;

(k) vitamins such as vitamin A and E, and vitamin alkyl esters, including those vitamin C alkyl esters;

(l) sunscreens such as octyl methoxyl cinnamate (Parsol MCX) and butyl methoxy benzoylmethane (Parsol 1789);

(m) phospholipids; and (n) mixtures of any of the foregoing components.

Finally a critical aspect of the invention is that the bar compositions comprise less than 5%, preferably less than 4, preferably less than 3%, more preferably less than 2%, more preferably less than 1% synthetic surfactant. The synthetic may be absent altogether.

The synthetic surfactant may be an anionic, nonionic, amphoteric or cationic surfactant or mixtures thereof and may be any one of hundreds of synthetic surfactants well know to those of ordinary skill in the art.

Typical examples are described in U.S. Pat. No. 3,723,325 to Parran Jr. and "Surface Active Agents and Detergents" (Vol. I & II) by Schwartz, Perry & Berch, both of which are also incorporated into the subject application by reference.

Other optional components which may be included in the bar composition of the invention include talc and glycerin.

The following examples are intended to further illustrate the invention and are not intended to limit the invention in any way.

Unless stated otherwise, all percentages are by weight.

EXAMPLES

Methodology

The following tests were used for evaluation of bars:

1. Perfume/Odor Evaluation

| Grading Scale | Definition |
|---|---|
| 1. Excellent | Meets standard |
| 2. Good | Approximates standard |
| 3. Fair | Noticeable deviation from standard |
| 4. Poor | Significant deviation from standard |
| 5. Unsatisfactory | Not recognizable as product |

Odor evaluations were conducted by trained perfumer. Bars were given an initial odor evaluation and were then stored as follows;

One bar stored for 1 week at RT (ca. 72° F.); one bar stored for 1 week at 80° F. and 80° relative humidity (R.H.); and one bar stored for 1 week at 105° F.

Similar tests were conducted at 2, 6 and 12 weeks.

At the specified times, the aged samples were evaluated by the perfumer for odor.

2. Sand/Slip Evaluation

Finished bars were evaluated for sand under 85° F. running water after firmly rotating bar for 50 turns. The following ratings applied:

| Perceivable Grit | Rating | Action |
|---|---|---|
| 0 hard particles: | Nil | Acceptable/Release |
| 1–2 hard particles: | Smooth | Acceptable/Release |
| 3–4 hard particles: | Slight | Need to consider further |
| 5–6 hard particles: | Moderate | Not-Acceptable |
| 7 hard particles: | Considerable | Not-Acceptable |
| 7+ hard particles: | Considerable + | Not-Acceptable |

"Slip" was evaluated using the same wash procedure as above. It was evaluated as "Good", "Fair" and "Poor".

This evaluation was done at both 75° F. and 85° F. in the pilot plant; only 85° F. in plant.

3. Color Evaluation

Principle

Color was measured in three dimensions: light/dark (white/black), red/green and yellow/blue. The appearance of a product depended on the contribution each dimension made. The tolerance in each dimension depends on the overall color of the product.

Each test sample was measured for color on the Macbeth Series 1500 with appropriate computer support. Each product has target values for lightness ("L"), red/green balance ("a"), and yellow/blue ("b") and, also, ranges for each dimension. Bars which have all three readings within the given ranges will have acceptable colors. The higher the "L" value, the whiter the color.

Instrumentation

Macbeth Series 1500 or 1500/Plus Spectophotometer

L, a, b 2 degree observer

Average 3 readings

Small aperture

Illuminant C (Northern Daylight)

Status—DOEIN or DREIS

D—Unit ceramic calibrated with specular component excluded

O—Reflection mode

E—Specular component excluded

I—Ultraviolet component included

N—Calibrated

R—Reflection mode

S—Calibrated

Calibration

The instrument was calibrated with the white ceramic title which was provided.

Standard Readings

The appropriate standard readings were entered for each brand.

Readings

Readings were taken by holding the bar surface firmly against the small aperture. Readings were taken of approximately the same region of the bar surface. To standardize this among the plants, the readings were taken just under the first letter in the product name. One reading for each bar is sufficient.

4. Lather Volume (Funnel Method)

Apparatus

Soap bars;

Two large sinks;

Measuring funnel. This was made by using a 10.5 inch diameter plastic funnel and a 100 mL graduated cylinder with the bottom cleanly removed. The cylinder was fitted with the 0 mL mark over the funnel stem. The cylinder was sealed to the funnel.

Reagents

Distilled water

Procedure

A. Fill sink

1. Place the funnel on the bottom of the sink #1.
2. Add distilled water to the sink until the 0 mL mark of the funnel is reached.

B. Generate lather

1. Run tap on sink #2;
2. Set temperature at 75° F., 95° F., or 105° F. as required;
3. Holding the bar between both hands under running water, rotate the bar for ten (10) half turns;
4. Remove hands and bar from under the running water;
5. Rotate the bar fifteen (15) half turns;
6. Lay the bar aside;
7. Work up lather for 10 seconds;
8. Place funnel over hands;
9. Lower hands and funnel into sink #1;
10. When hands are fully immersed, slide from under the funnel;
11. Lower funnel to the bottom of the sink;
12. Read the lather volume;
13. Remove the funnel with lather from sink #1;
14. Rinse funnel and hands in skin #2;

Note: The water in sink #1 was used for a whole series of readings. A trained expert carried out the evaluation.

Examples 1–3 and Comparative: Effect of Weak Electrolyte

Comparative:

Applicants extruded and plodded a bar with the following formulation:

| Ingredient | % by Wt. |
|---|---|
| Soap (64/36) | 73.4 |
| C16–C18 fatty acid | 12.8 |
| "Strong" electrolyte (NaCl or a combination of MgCl2/NaCl) | 0.7 |
| Perfume, preservative | Minors, (e.g., 0.1) |
| $H_2O$ | To balance |

The bar had no non-soap surfactant.

Bar was made by mixing ingredients at a temperature of about 200° to 230° F., cooling to form chips and plodding chips to form bar.

The bar made good noodling throughput and good noodles although it was slightly sticky. Lather volume (measured in cc using methodology described above) was 110 cc. The bar had score of 4 in odor evaluation test (indicating a "poor" odor (fatty) well outside of normal product specifications) and weak perfume. The bar also had a poor "L" value (80.59) after two week color evaluation (the lower the "L", less white the bar) and poor to fair slip characteristics.

Examples 1–3

Another bar (Example 1) similar to the comparative bar was prepared having 71.9% soap (60/40), 12.5% C16–C18 fatty acid, 0.7 "strong" electrolyte, 10.9% water, and additionally comprising 2.1% organic salt (i.e., sodium isethionate).

The comparative bar, the bars of Examples 1–3 (having 2%, 5% and 7% sodium isethionate, i.e., AIT) and a control Lever 2000® bar having 54.6% soap, 4.8% C16–C18 fatty acid, 2% C8–C14 fatty acid, 0.6% "strong" electrolyte, 10.5% water, 5.6% sodium isethionate and 20.3% non-soap surfactant (compared to 0% in comparative and Examples 1–3) were compared for odor, color and sand/slip and results are set forth in Tables 1–3 below.

TABLE 1

Odor Evaluation

Initial Odor Evaluations

| | |
|---|---|
| Comparative - No AIT* | 4 fatty/perfume weak |
| Example 1 - 2% AIT | 4 fatty/perfume weak |
| Example 2 - 5% AIT | 2/perfume weak |
| Example 3 - 7% AIT | 2/product base odor |
| Lever 2000(R)** | 2/product specification |

*Outside invention because of no weak electrolyte;

**Outside invention because has more than 5% synthetic surfactant.

It can be seen that addition of organic salt (i.e., sodium isethionate, AIT) results in lower score (from 4 to 2) indicating acceptable standard.

TABLE 2

| Color Evaluation | | | | | | | | | |
|---|---|---|---|---|---|---|---|---|---|
| Aging Data - 2 wk MacBeth | RT | | | 80/80 | | | 105° F. | | |
| | L | A | B | L | A | B | L | A | B |
| Comparative No AIT | 80.31 | −2.86 | 5.58 | 81.85 | −2.65 | 4.82 | 80.59 | −2.96 | 6.23 |
| Example 1 - 2% AIT | 90.10 | −2.22 | 6.01 | 89.71 | −2.04 | 5.28 | 89.44 | −2.15 | 6.25 |
| Example 2 - 5% AIT | 90.37 | −2.20 | 6.19 | 91.17 | −1.98 | 5.14 | 90.61 | −2.29 | 6.65 |
| Example 3 - 7% AIT | 92.71 | −1.73 | 5.67 | 93.33 | −1.56 | 4.74 | 92.91 | −1.86 | 6.44 |
| Control Lever 2000 | 92.56 | −1.56 | 5.91 | 92.85 | −1.46 | 5.31 | 92.11 | −1.54 | 6.74 |

TABLE 3

| Aging Data - Sand/Slip: through 8 week (0% AIT through 7% AIT) | | | | | | |
|---|---|---|---|---|---|---|
| | RT/75F | RT/85F | 105/75F | 105/85F | 8080/75F | 8080/85F |
| Comparative | nil/poor | slight/poor | Mod/fair | mil/poor | nil/fair | mod/poor |
| Example 1 (2% AIT) | nil/fair | nil/fair | Mod/fair | slight/fair | nil/fair | nil/fair |
| Example 2 (5% AIT) | slight/fair | nil/good | Mod/good | nil/good | nil/fair | nil/fair |
| Example 3 (7% AIT) | nil/good | nil/good | Slight/fair | slight/fair | nil/good | nil/good |
| Lever 2000 ® | nil/good | nil/good | nil/good | nil/good | nil/good | nil/good |

As seen from Table 1, addition of organic salt electrolyte improved odor scores from a "poor" score of 4 (for no electrolyte or 2% electrolyte) to an accepted "good" standard of 2 (as in Lever 2000®).

Further, as seen in color evaluation using MacBeth Test, addition of organic salt significantly improved whiteness (increase in "L" value) at all temperature beginning at even 2% salt level.

Finally, as seen in Table 3, addition of organic salt also improved sand/slip properties. That is, there are no poor slip or moderate sand/slip ratings.

It is simply unexpected that addition of organic salt to superfatted bars would remarkably enhance consumer properties, particularly since high electrolyte/salt levels are normally associated with very brittle bars having high cracking. Addition of fatty acid alleviates this problem when organic salts are used.

Comparative Examples 2 and 3 and Example 5–7: Minimum Fatty Acid

Comparative 2 (Bar with Organic Salts but no Fatty Acid)

As noted, it is a critical aspect of the invention that at least 4% free fatty acid be used (i.e., the organic salt is added to a superfatted soap and not just a soap base having little or no free fatty acid).

Thus, for example, a composition with 82% soap (60/40), 7% sodium isethionate, 0.7% strong electrolyte, 10.6–18.1% water and no non-soap surfactant or fatty acid (i.e., there is no fatty acid as required by the invention) was not processable. The noodling resulted in poor (dry/crumbly) material. Soap was too short (e.g., grain) and unprocessable) to even process into a bar. Applicants were able to force production of bar at 18.1% moisture but material was draggy; also soap logs fell apart coming out of the plodder, and material boiled over in hot mix stage (an indication of shortness). Finally, the bar had poor slip properties and water was an unstable structurant at this high level.

Example 5 (Organic Salt Plus 4% Stearic Acid)

When 7% isethionate and 4% free fatty acid (stearic acid) was added to Comparative bar 2, applicants were able to plod bar at 15.1% moisture. However, throughput was poor, slip was "fair", noodles were powdery and soap felt "short" (e.g., grainy).

Comparative 3 (Organic Salt Plus 4% Coconut)

When bar with 7% isethionate and 4% coconut fatty acid was used, 14.1% moisture was needed to process. Further, material could not be processed through plodder using cold (about 40–60° F.) water on barrels and barrels had to be heated up to get bar out. Material was soft, brittle and "short". There was poor throughput and slip was judged only as "fair".

Example 6 (7% Isethionate Plus 7% Acid)

When bar with 7% isethionate and 7% stearic acid was used (ratio of 1:1) instead of 4% stearic, it was crumbly, but had much better processing than bar with 4% fatty acid. The bar material was firm and had good throughput. Further, the bar had good odor and slip properties and was processable.

Example 7 (7% Isethionate Plus 10% Fatty Acid)

When 7% isethionate and 10% stearic acid were used (fatty acid/isethionate ratio of greater than 1:1) processing (measured as log throughput) was very good.

Table 4 below highlights throughput (7% isethionate, constant moisture of 10%) as function of stearic acid level.

TABLE 4

| % Stearic Acid | Log Throughput (lbs./min) |
|---|---|
| 0% | Could not process |
| 4% | Could not process |
| 7% | 7 |
| 10% | 11 |
| 12% | 13 |

Essentially this Table shows that while minimum 4% fatty acid (preferably stearic) is needed according to invention (Example 5), ratio of fatty acid to isethionate is preferably 1:1 or greater (see Examples 6 and 7).

Sodium Citrate Example—Example 8

Odor Improvement w/Sodium Citrate (Both bars contain 0.8% TiO2)

| | |
|---|---|
| Comparative - No Citrate or AIT w/12% fatty acid | 4 fatty/perfume weak |
| 6% Na-Citrate w/10% fatty acid | 2/product specification |

Color Improvement w/Sodium Citrate (Both bars contain 0.8% TiO2)

| | | | |
|---|---|---|---|
| Comparative - No Citrate or AIT w/ 12% fa | L: 80.31 | a: −2.86 | b: 5.58 |
| 6% Na-Citrate w/10% fatty acid | L: 93.04 | a: −1.68 | b: 5.63 |

Increase in the "L" whiteness value indicates an improvement in bar color.

Sodium Citrate performs a similar improvement in odor/ color profile.

Comparatives 4 and 5

In order to show the negative effect of certain elecrolytes (e.g., NaCl) in predominantly soap bar compositions (e.g., their known tendency to cause brittle, "cracked" bars which are difficult to process) applicants prepared soap bar compositions containing free fatty acid (superfatted) and electrolyte (e.g., NaCl).

The following Comparative compositions was prepared:

| Ingredient | % by Wt. |
|---|---|
| 64/36* Neat Soap | 78.71 |
| Free Fatty Acid (Stearic Acid) | 6.00 |
| NaCl** | 3.00 |
| Preservatives | 19 |
| TiO2 | 0.80 |
| Perfume | 1.30 |
| Water | 10.00 |

*Tallow to coconut fatty acid ratio
**Ratio of free fatty salt to salt was 6:3 or 2:1

The ingredients were mixed at a temperature of about 200 to 230° F., dried, flaked on a mill, and then extruded through the plodder at RPM of about 9.5 at about a temperature of 75° F.

The following Comparative composition was also prepared:

| Ingredient | % by Wt. |
|---|---|
| 64/36* Neat Soap | 72.71 |
| Free Fatty Acid (Stearic Acid) | 12.00 |
| NaCl | 3.00 |
| Preservatives | 19 |
| TiO2 | 0.80 |
| Perfume | 1.30 |
| Water | 10.00 |

This composition was same as previous except that ratio of FFA to salt was 12:3 or 4:1 here.

The second formulation was prepared and plodded at same rate as first.

Both examples were evaluated as set forth below:

| Formulation | Log Extrusion Throughput (lb/min) | Sand/Slip Rating | Comment |
|---|---|---|---|
| 3% Sodium Chloride, 12% Stearic Acid (4:1 FFA:Inorganic Salt) | 1.1 | Moderate/ Fair | Fair Slip & Fine Pumice |
| 3% Sodium Chloride, 6% Stearic Acid (2:1 FFA:Inorganic Salt) | Unprocessable (Could not form log, i.e., billets crack out of plodder) | Consider-able/ Fair* | Could not extrude (Brittle/Short) |

*This rating was produced by taking pieces of the broken cracked logs coming out of the plodder and pressing them under high pressure to force them into the shape of a bar.

These examples demonstrate the undesired "shortening" effects of inorganic strong electrolytes (salts) in superfatted bar soap formulations. Such formulations are not acceptable on the basis of throughput. Sodium isethionate (organic salt/electrolyte) does not demonstrate this behavior, and also improves the sand/slip characteristics of the finished bars. Sodium chloride does not have this desirable effect of enhancing bar user characteristics.

What is claimed is:

1. An extruded bar composition comprising:

(a) 50% to 80% by wt. soap;

(b) 4% to 35% by wt. free fatty acid;

(c) 1% to 10% by wt. of an organic salt selected from the group consisting of alkali metal isethionate, alkali metal citrate, alkali metal acetate, organic salt of aspartic acid, organic salt of D-gluconic acid, alkali metal gluceptate and mixtures thereof;

(d) about 10% by wt. water;

wherein said composition has less than about 4% synthetic surfactant and wherein said bar is processed using standard processing equipment in which said bar is made by mixing ingredients, drying and extruding.

2. A composition according to claim 1, comprising 55% to 80% soap.

3. A composition according to claim 1, wherein fatty acid is C8–C22.

4. A composition according to claim 3, wherein fatty acid is C12–C18.

5. A composition according to claim 4, wherein fatty acid is C16–C18.

6. A composition according to claim 3, comprising 6% to 25% free fatty acid.

7. A composition according to claim 6, comprising 6 to 20% free fatty acid.

8. A composition according to claim 1, wherein said organic salt is alkali metal isethionate.

9. A compositions according to claim 1, wherein ratio of fatty acid to organic salt is 1:1 and higher.

* * * * *